United States Patent [19]

Magasi

[11] Patent Number: 4,826,492
[45] Date of Patent: May 2, 1989

[54] MEDICAL PROBE

[75] Inventor: Josef Magasi, Sandhausen, Fed. Rep. of Germany

[73] Assignee: Hospal Ltd., Switzerland

[21] Appl. No.: 1,770

[22] Filed: Jan. 9, 1987

[30] Foreign Application Priority Data

Jan. 10, 1986 [DE] Fed. Rep. of Germany ....... 3600496

[51] Int. Cl.⁴ .............................................. A61M 5/32
[52] U.S. Cl. ..................... 604/274; 604/272
[58] Field of Search ....................... 604/177, 272, 274

[56] References Cited

U.S. PATENT DOCUMENTS

| | | | |
|---|---|---|---|
| 3,119,391 | 1/1964 | Harrison | 604/274 |
| 3,831,814 | 8/1974 | Butler | 604/274 |
| 3,906,932 | 9/1975 | Ayres | 604/274 |
| 4,287,891 | 9/1981 | Peters | 604/905 |
| 4,352,354 | 10/1982 | Ujihara | 604/177 |
| 4,496,353 | 1/1985 | Overland | 604/272 |
| 4,585,446 | 4/1986 | Kempf . | |

FOREIGN PATENT DOCUMENTS

| | | | |
|---|---|---|---|
| 0158697 | 6/1984 | European Pat. Off. . | |
| 2929886 | 1/1981 | Fed. Rep. of Germany | 604/177 |
| 2258764 | 8/1975 | France | 604/177 |

Primary Examiner—C. Fred Rosenbaum
Assistant Examiner—Kathleen Daley
Attorney, Agent, or Firm—Finnegan, Henderson, Farabow, Garrett & Dunner

[57] ABSTRACT

A needle type probe having a displacement surface acting as a bridge which extends across the aperture into the lumen of the needle. The displacement surface defines two approximately equal lateral openings on either side of the bridge and acts to displace and stretch the skin about the needle shank. A holder for the needle type probe is provided which comprises a sleeve which is pushed over the shank of the needle with a force fit, the sleeve having a stopper portion at the end towards the needle point and a holder plate rotatably mounted on the sleeve by means of a collar which is fit over the sleeve. The stopper portion and the front edge of the holder plate collar each have a serrated surface for selectively restricting rotational movement of the collar relative to the sleeve and needle shank. There is further provided a method for making a needle type probe of the instant invention wherein a point wise force is exerted on a tubular needle material at its front edge and the end of the tube is collapsed onto itself until contact is made between radially opposite inner portions of the inner surface of the needle shank. The shank is then ground rearwardly from the contact point to form a bridge extending from the needle point rearwardly with openings on either side of the bridge.

20 Claims, 3 Drawing Sheets

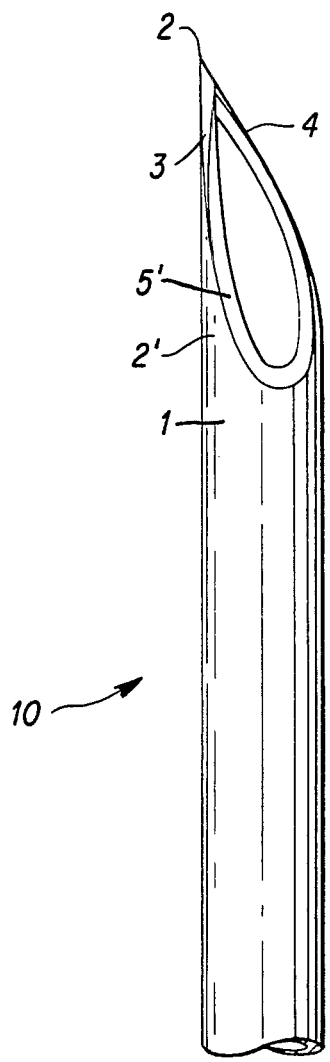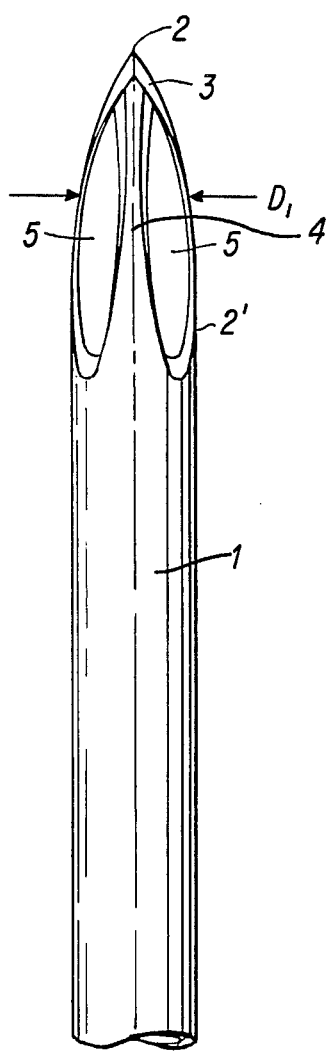

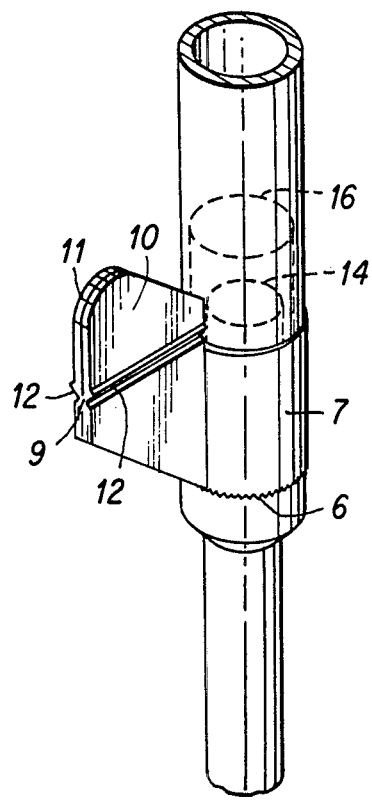
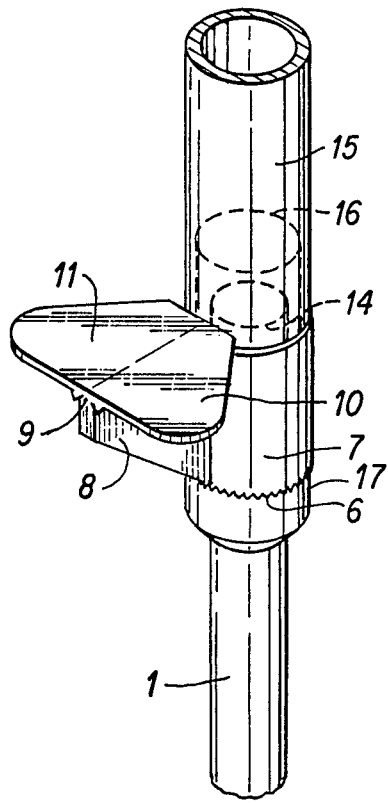

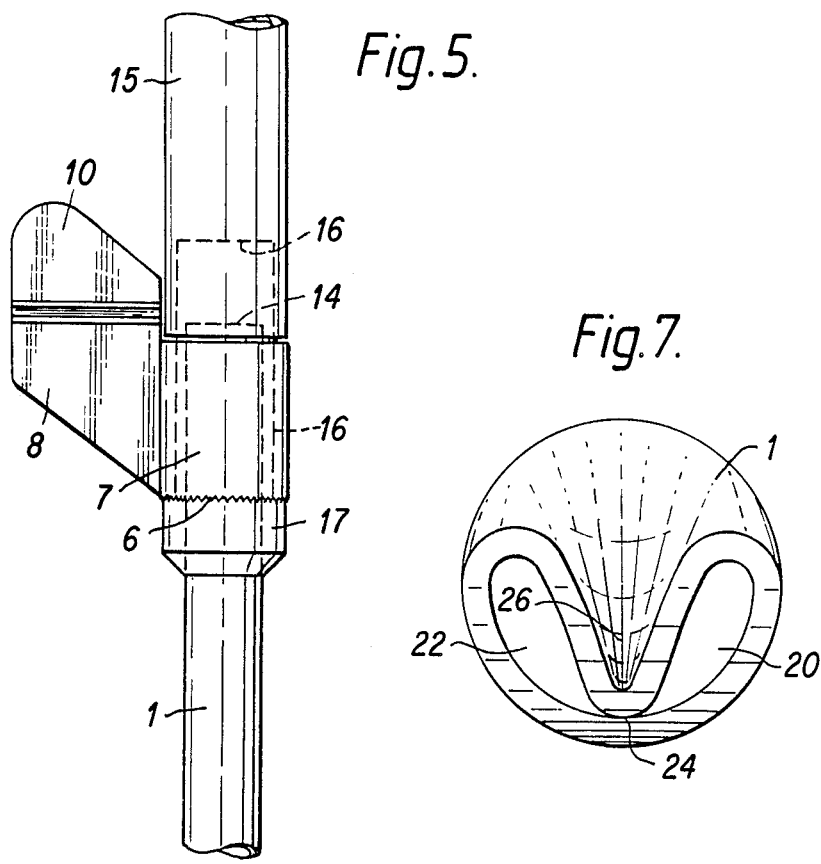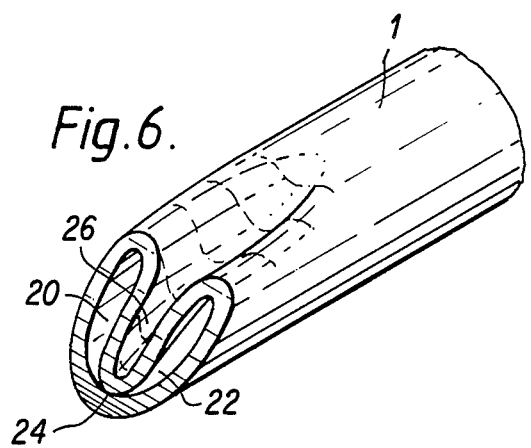

MEDICAL PROBE

BACKGROUND OF THE INVENTION

1. Field of the Invention

The present invention relates to a medical probe for accessing the interior of a volume defined by a puncturable material, and more particularly to a needle-type probe insertable through a patient's skin.

2. Description of the Related Art

Prior art needle probes are used, for instance in human medicine, for the direct venipuncture of arteriovenous fistulas, or for venipuncture of fairly large blood vessels for intermittent chronic hemodialysis or for extraction of fairly large quantities of blood from a patient.

Such needles are described in German Pat. Nos. 22 59 865 and 22 59 866. These prior art needles have a sharp, smooth cutting edge for the percutaneous puncture of blood vessels where a traumatism of the skin tissue of the patient is largely suppressed. The cutting edge of these needles creates an arcuate incision in the patient's skin which creates a skin flap defined by the parimeter of the arcuate incision. In order to insert the prior art needles through the patient's skin, a greater pressure must be applied to the patient's skin to create the initial incision than is necessary to insert the needle into the blood vessel below the skin. This higher pressure during initial incision of the needle causes discomfort and pain for the patient. These prior art venipuncture type needles have a large lumen diameter in relation to the needle wall thickness, since up to 300 mililiters of blood per minute at rates up to 4 meters per second must be passed through the needle lumen.

These prior art needles have an open, oblique ground edge acting as a cutting surface and as a rule, a small opening immediately rearward of the puncturing tip which serves to equalize pressure on the inner and outer surfaces of the needle aperture when inserted in a patient's blood vessel. This equalization of pressure acts to prevent the wall of the blood vessel from being sucked onto the ground edge opening and preventing flow through the aperture into the lumen of the needle. However, the necessity for providing the opening increases the cost of manufacture of the needle.

With these prior art needles, patients are subjected to venipuncture for the purpose of hemodialysis more than one hundred times per year, thus requiring numerous incisions to be made through a small area of the patient's skin since only relatively small blood vessels are available for the hemodialysis. As discussed above, upon puncturing of the patient's skin with the prior art needles an arcuate cut is created. It frequently happens that the skin flap formed by the periphery of the arcuate cut is picked up during puncture by the upper edge of the needle opposite the ground edge cutting surface and is drawn into the cut. This results in scarring of the skin tissue where the incision is made. The subsequent healing of the scarred skin tissue results in a thickening of that area of the skin thus impeding a further puncture into that tissue zone. Moreover, the arcuate cut formed in the patient's skin by the incision of the needle does not allow for a tight fit of the skin around the needle shank as the needle is inserted into the patient's body. The resulting loose fit of the patient's skin around the needle shank allows for seepage of the blood through the arcuate incision around the needle shank.

The prior art needles described above normally include a holder for a technician to guide the needle onto the patient's skin and blood vessel without obstructing the view onto the puncture point. The needle is normally rotatably mounted in this holder. Unfortunately, during puncture of the patient's skin, it frequently happens that the needle is unintentionally rotated in the holder and thus causes traumatisms to the patient's skin at the insertion point into the blood vessel since the ground edge cutting surface is not properly oriented. Moreover, improper orientation of the needle impedes the flow of blood into the needle lumen.

It is therefore an object of the present invention to provide a probe for insertion through a patient's skin which creates a reduced length of the incision line thus reducing the required pressure on the probe to puncture the patient's skin and reducing the amount of discomfort and pain felt by the patient during insertion.

It is a further object of the present invention to provide a probe for incision through a patient's skin which utilizes the natural elasticity of human skin to stretch the skin around the incision parameter about the periphery of the probe shank thus creating a tight fit of the skin around the shank and eliminating seepage of blood through the incision.

It is a further object of the present invention to provide a holder for a needle probe which selectively restricts rotational movement of the probe when inserted in a patient's body.

It is still a further object of the present invention to provide a method of manufacturing the needle probe of the instant invention.

Additional objects and advantages of the invention will be set forth in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

To achieve the foregoing objects, and in accordance with the purposes of the invention as embodied and broadly described herein, a probe for accessing the interior of a volume having an exterior surface of elastic, puncturable material is provided which comprises a hollow shank having a nose portion at the distal end, the nose portion having a bottom portion defining a puncturing tip of the probe. The nose portion further comprises inclined sidewalls extending rearwardly and upwardly from the puncturing tip and defining at least one aperture into the hollow shank, the aperture into the hollow shank being inclined relative to the central axis of the hollow shank. A displacement surface, bridging the shank and the nose portion, is provided which extends from the rearward portion of the aperture and terminates acts to displace and stretch the elastic, puncturable material about the outer periphery of the shank as the nose portion penetrates the puncturable material.

Preferably, the bottom portion of the nose portion includes beveled ground edges extending rearwardly and outwardly from opposite sides of the puncturing tip and terminating a predetermined distance apart at respective ones of the sidewalls of the nose portion. The predetermined distance is selected to be less than the external diameter of the hollow shank. It is further preferable that the displacement surface terminates substantially tangential to the beveled ground edges.

It is still further preferable that the displacement surface bridging the shank and the bottom portion of the probe is configured with a longitudinally directed indentation therein for directing fluid flowing from the volume defined by the exterior surface of elastic, puncturable material, through the lateral openings and into the hollow portion of the shank.

In accordance with the invention and as embodied and broadly described herein there is further provided a holder for a venipuncture needle, the needle having a hollow tubular shaft portion. The holder comprises a tubular sleeve dimensioned to snugly fit over the proximate end of the tubular shaft. The sleeve has a stopper portion configured with an external diameter larger than the remainder of the sleeve, and the upper surface edge portion of the stopper is serrated. A tubular collar is configured to rotatably fit over the sleeve with the collar having a holder plate extending radially from the collar for gripping by an operator or technician to rotatably adjust the needle. The front edge portion of the collar has a serrated surface for engaging the serrated surface of the upper edge of the stopper portion of the sleeve. In this manner, the engaged serrated surfaces selectively restrict rotation of the collar relative to the sleeve and needle shank when the needle is inserted through a patient's skin.

In accordance with the invention and as embodied herein, there is further provided a method for manufacturing a needle-type probe having a displacement surface bridging the opening into the lumen of the probe. The method comprises the steps of forcing a point on the interior front edge surface of a tubular, hollow shank section into contact with a radially opposite interior edge portion of the shank to thereby create a substantially V-shaped channel on the outer periphery of the shank section. The V-shaped channel defines a pair of substantially tear-shaped openings at the end of the shank which lead into the hollow lumen of the shank. Next, the tubular, hollow shank section is ground rearwardly from the contact point of the radially opposite inner edge portion and the interior front edge surface of the shank to form a pair of inclined, lateral apertures from the tear-shaped openings. Through this grinding process a displacement surface is formed from the V-shaped channel which extends rearwardly from the contact point.

BRIEF DESCRIPTION OF THE DRAWINGS

The accompanying drawings, which are incorporated in and constitute a part of the specification, illustrate a preferred embodiment of the invention and, together with the general description given above and the detailed description of the preferred embodiment given below, serve to explain the principles of the invention.

FIG. 1 is a side view of a needle-type probe incorporating the teachings of the present invention;

FIG. 2 is a top view of the probe illustrated in FIG. 1;

FIG. 3 is an isometric view of a holder for a needle-type probe with the flap portions of the holder in a folded position;

FIG. 4 is an isometric view of the holder of FIG. 3 with the flaps in an unfolded position;

FIG. 5 is a side view of the holder of FIG. 3;

FIG. 6 is an isometric view of the hollow tubular shank section illustrating the method of manufacture of the probe of FIG. 1; and FIG. 7 is a front view of a hollow tubular shank section illustrating the method of manufacture of the probe of FIG. 1.

DESCRIPTION OF THE PREFERRED EMBODIMENT

Reference will now be made in detail to the present preferred embodiment of the invention as illustrated in the accompanying drawings.

In accordance with the present invention there is provided a probe for accessing the interior of a volume having an exterior surface of elastic, puncturable material. The probe comprises a hollow shank having a nose portion at the distal end. The nose portion has a bottom portion configured as a puncturing tip of the probe, and inclined sidewalls extending rearwardly and upwardly from the puncturing tip and defining at least one aperture into the hollow shank. The aperture is inclined relative to the central axis of the hollow shank.

As shown in FIGS. 1 and 2, a probe generally referred to by numeral 10, includes a hollow shank 1 having a nose portion at the distal end thereof. The nose portion includes a puncturing tip 2 and sidewalls 2' extending rearwardly and upwardly from the puncturing tip 2. The sidewalls 2' define an inclined aperture 5 leading into the lumen of the hollow shank. The bottom portion of the nose portion includes beveled ground edges 3 extending rearwardly and outwardly from opposite sides of the puncturing tip 2. The beveled ground edges 3 terminate at the side walls 2' of the nose portion. These beveled ground edges 3 serve as the cutting edge of the probe when being inserted in a patient's skin. The ground edges terminate a discreet distance apart represented by D1 in FIG. 2. The discreet distance D1 is selected to be less than the external diameter of the hollow shank 1. The sidewalls 2' further include beveled top portions 5' which partly overlap the beveled ground edges 3 where the ground edges terminate in the sidewalls 2'.

As embodied herein a displacement surface, bridging the shank and the bottom portion of the probe, extends from the rearward portion of the aperture and terminates substantially at the puncturing tip. The displacement surface acts to displace and stretch the elastic, puncturable material about the outer periphery of the shank as the nose portion penetrates the puncturable material.

With continued reference to FIGS. 1 and 2, a displacement surface 4 bridges the shank and the bottom portion of the probe across the aperture 5. The displacement surface 4 extends from the rearward portion of the aperture 5, along the central axis of shank 1, and terminates substantially tangential to the bottom portion of the nose portion of the probe near the puncturing tip 2. The terminal end of the bridge 4 is attached to the forwardmost portion of the probe 10 at the bottom portion preferably by means of laser beam welding, or by any other conventional means wherein the displacement surface 4 can be attached to the bottom portion of the nose portion. The terminal end of displacement surface 4 is substantially tangential to the bottom portion of the nose portion to provide smooth displacement of the puncturable material onto the displacement surface 4 from the puncturing tip 2 and cutting edge of the nose portion. The displacement surface 4, by bridging the shank and the bottom portion across the aperture 5, creates two distinct lateral openings into the lumen of the shank 1. These openings are preferably inclined relative one another towards the forwardmost point of each opening and are generally tear-shaped in configuration as shown in FIG. 2.

The displacement surface 4, acting as a bridge, lifts and stretches the puncturable, elastic material cut by puncturing tip 2 and beveled ground edges 3 onto the shank section 1 as the nose portion of the probe penetrates the puncturable material. By way of example and not limitation, the puncturable, elastic or an organ of a patient. In this manner, the skin is stretched and displaced about the outer periphery of the shank 1 thus creating a tight fit of the skin about the shank 1 to prohibit seepage of fluid from the volume around the outer periphery of the shank.

The incision into the elastic skin created by the puncturing tip 2 and beveled ground edges 3 is in the form of a substantially straight line, as opposed to the arcuate incision created by prior art venipuncture needles or probes. The substantially straight line incision is formed because the spacing of the beveled ground edges 3 is selected to be less than the diameter of the shank 1. Thus, the incision created by the instant invention has a length approximately 30 percent smaller than the arcuate incisions caused by prior art venipuncture needles or probes. This results in less damage to nerve endings in a patient's skin, less pressure required to make the initial incision through the patient's skin, and less damage to the tissue of the skin thus reducing the amount of scar tissue formed after the probe is removed from the patient.

Displacement surface 4 is configured with a longitudinally directed indentation therein for directing blood flowing from the patient's vessel into the lumen of the hollow shank 1. In this manner, there is no stagnation point created immediately in front of the displacement surface 4 around the puncturing tip 2.

The use of the probe 10 constructed in accordance with the instant invention is not limited to venipuncture type needles, but may also be applied to needle-type probes used for intra-muscular injection. When used for intra-muscular injection, the needle according to the present invention provides enhanced diffusion of the solution being injected into the muscle since the solution flows through multiple openings on either side of the displacement surface. Moreover, needle-type probes constructed in accordance with the present invention are not limited to a single bridge 4 across the aperture 5, and a plurality of bridges may be formed to enhance the stretching and displacing action of the elastic, puncturable material about the shank 1. A probe according to the present invention may also be used for sampling tissue of an internal organ of a patient as in a biopsy procedure.

As embodied herein, the probe 10 is preferably constructed of corrosion resistant metal, such as stainless steel. However, the probe 10 may also be constructed of a synthetic material, such as plastic. The probe 10 may also be constructed of a combination of synthetic material and corrosion resistant metals.

In accordance with the present invention there is also provided a holder for a venipuncture needle constructed in accordance with the probe 10. The holder comprises a tubular sleeve dimensioned to snugly fit over the proximate end of the tubular shaft of the venipuncture needle. The sleeve has a stopper portion configured with an external diameter larger than the remainder of the sleeve. The upper surface edge of the stopper portion is serrated. The holder further includes a tubular collar configured to rotatably fit over the sleeve with the collar having a holder plate extending radially from the collar for gripping by an operator or technician to hold and adjust the needle. The front edge portion of the collar has a serrated surface for engaging the serrated surface of the upper edge of the stopper portion of the sleeve. The engagement of these serrated surfaces allows for selective rotation of the collar relative to the sleeve when the needle is inserted through a patient's skin.

As embodied herein and shown in FIGS. 3 and 4, a sleeve 16 having a stopper portion 17 is fit over the distal end 14 of the needle shank 1. The upper surface of the stopper portion has a serrated edge 6 which engages with the serrated front edge surface 6 of tubular collar 7. Tubular collar 7 is dimensioned to fit over sleeve 16. Collar 7 has a holder plate 8 extending radially therefrom for gripping by a technicial to hold and adjust the needle shank 1 relative to the sleeve 16. Serrated surfaces 6 of collar 7 and stopper portion 17 engage one another to selectively restrict rotation of the collar 7 relative to the sleeve 16 and needle shank 1 when the needle is inserted through a patient's skin.

With reference to FIG. 5 and continued reference to FIGS. 3 and 4, the holder further includes two flaps 10 and 11 rotatably mounted on the top surface portion 9 of holder plate 8. Flaps 10 and 11 are in a folded state shown in FIG. 3 wherein the flaps are substantially parallel to the holder plate 8, and in an unfolded state in FIG. 4 wherein the flaps 10 and 11 extend substantially perpendicular to holder plate 8 on each side of the holder plate 8. Each flap 10 and 11 has a beveled edge portion 12 extending along the base thereof which engages with a mating channel 9 configured on either side of the top surface portion of the holder plate 8 when the flaps are in the unfolded state.

Collar 7 engages stopper portion 17 at serrated edges 6 by means of tubing 15 which is fit over the distal end of the sleeve 16 and contacts the distal end of the collar 7 to push serrated surface 6 of collar 7 into contact with serrated surface 6 of stopper portion 17.

The holder described above allows for a technician to grasp the holder plate 10 and flaps 10 and 11 in an unfolded position between the thumb, index and middle fingers. The serrated edges 6 of stopper portion 17 and collar 7 acts to restrict rotational movement between the shank 1 and the holder 8 while the needle is inserted in the patient's blood vessel. With the needle removed from the patient's arm, the operator can readily adjust the rotational position of the holder and shank 1 by disengaging the serrated portions 6 of the stopper portion 17 and the collar 7.

In operation blood is withdrawn from the patient's vessel through the needle shank 1 and passes into the tubing 15 where it may be collected in any adequate receptacle. The collar 7 may also be fixed on the sleeve 16 by means of a ring inserted over the distal end of the sleeve 16 to push collar 7 against stopper portion 17.

In accordance with the invention there is also provided a method for manufacturing a needle-like probe having a displacement surface bridging the opening into the lumen of the needle. The method comprises the steps of forcing a point on the interior front edge surface of a tubular hollow shank section into contact with the radially opposite inner edge surface of the shank section to thereby create a substantially V-shaped channel on the outer periphery of the shank section. The V-shaped channel defines a pair of substantially tear-shaped openings into the hollow shank. Next, the shank section is ground rearwardly from the contact point between the interior front edge surface of the front edge portion and the radially opposite inner edge surface to form a pair of inclined, lateral apertures from the tear-shaped openings and a displacement surface from the V-shaped channel. The displacement surface extends rearwardly from the contact point.

As embodied herein and shown in FIGS. 6 and 7, the end of the shank section 1 is collapsed onto itself to thus form longitudinal channel 26 and tear-shaped openings 20 and 22 on either side of contact point 24 of the inner surface of the shank section 1. The shank section is then machine ground rearwardly from contact point 24 at an angle to thus form lateral openings 20 and 22 and a displacement surface 4 from the V-shaped channel 26. Preferably bevels are formed at the inner edges of each lateral opening. The portion of the shank immediately adjacent the contact point 24 is ground into bevels to form puncturing tip 2 and beveled ground edges 3 as shown in FIG. 1.

Additional advantages and modifications will readily occur to those skilled in the art. The invention in its broader aspects is, therefore, not limited to the specific details, representative apparatus and illustrative example shown and described. Accordingly, departures may be made from such details without departing from the scope of the invention as defined by the appended claims and their equivalents.

What is claimed is:

1. A probe for accessing the interior of a volume having an exterior surface of elastic, puncturable material, comprising:
    a hollow shank having a nose portion at the distal end, said nose portion having a bottom portion defining a puncturing tip of said probe, and sidewalls extending rearwardly and upwardly from said puncturing tip and defining at least one aperture into said hollow shank; said aperture being inclined relative to the central axis of said hollow shank; and
    a non-cutting displacement surface, bridging said shank and said bottom portion, extending from the rearward portion of said aperture along a smoothly inflected path and terminating substantially tangentially at said puncturing tip for displacing and stretching said elastic, puncturable material about the outer periphery of said shank as the nose portion penetrates the puncturable material.

2. The probe of claim 1, wherein said bottom portion of said nose portion includes beveled ground edges extending rearwardly and outerwardly from opposite sides of said puncturing tip and terminating a predetermined distance apart at respective ones of said side walls of said nose portion, said predetermined distance selected to be less than the external diameter of said hollow shank.

3. The probe of claim 2, wherein said sidewalls have a beveled top portion which partly overlaps said beveled ground edges where said ground edges terminate at said sidewalls.

4. The probe of claim 2, wherein said displacement surface terminates substantially tangential to said bottom portion of said nose portion.

5. The probe of claim 4, wherein the terminal end of said displacement surface is beam welded to said bottom portion of said nose portion.

6. The probe of claim 2, wherein said displacement surface splits said inclined aperture into first and second lateral openings, the periphery of each said lateral opening being defined by respective ones of said beveled ground edges, said beveled top portions of said sidewalls and the edges of said displacement surface.

7. The probe of claim 6, wherein said displacement surface is configured with a longitudinally directed indentation for directing fluid flowing from said volume defined by said exterior surface of puncturable material through said lateral openings and into the hollow portion of said shank.

8. The probe of claim 1, wherein said hollow shank, said nose portion and said displacement surface are made of corrosion resistant metal.

9. The probe of claim 1, wherein said displacement surface is made of synthetic material.

10. The probe of claim 1, wherein said nose portion of said probe and said displacement surface are made of synthetic material.

11. A venipuncture needle for withdrawing blood from a blood vessel of a patient, comprising:
    a hollow tubular shank having a nose portion at the distal end, said nose portion having a bottom portion defining a puncturing tip of said needle, said puncturing tip having beveled ground edges extending rearwardly and outwardly from opposite sides of said puncturing tip and terminating at beveled sidewalls extending rearwardly and upwardly to form an aperture into the hollow lumen of said needle, said aperture being inclined relative to the longitudinal axis of said needle shank; and
    a non-cutting displacement surface forming a bridge over said inclined aperture to split said inclined aperture into first and second lateral openings, said displacement surface extending forwardly and downwardly from the rearwardmost end of said inclined aperture along a smoothly inflected path and terminating substantially tangentially to said ground edges of said puncturing tip, said displacement surface acting to displace and stretch the skin and said blood vessel about the tubular shank of said needle as said puncturing tip penetrates the punctured skin and the blood vessel of the patient.

12. The venipuncture needle of claim 11, wherein said ground edges of said puncturing tip terminate at said sidewalls of said nose portion, the terminal ends of each said ground edge being separated by a predetermined distance selected to be less than the outer diameter of said tubular shank of said needle.

13. The venipuncture needle of claim 12, wherein said displacement surface is configure with a longitudinally directed indentation therein for directing blood flowing from said blood vessel through said lateral openings and into the hollow lumen of said shank of said needle.

14. A holder for a venipuncture needle, said needle having a hollow tubular shank, comprising:
    a tubular sleeve dimensioned to snugly fit over the proximate end of said tubular shank; said sleeve having a stopper portion configured with an external diameter larger than the remainder of said sleeve, the upper edge portion of said stopper having a serrated surface; and
    a tubular collar configured to rotatably fit over said sleeve, said collar having a holder plate extending radially from said collar for gripping to rotatably adjust said needle, and the front edge portion of said collar has a serrated surface for engaging said serrated surface of said upper edge of said stop portion of said sleeve for selectively restricting rotation of said collar relative to said sleeve and said needle shank when said needle is inserted through a patient's skin.

15. The holder of claim 14, wherein said holder plate includes two flaps rotatably mounted on the top surface portion of said holder, said flaps having a folded state substantially parallel to said holder plate, and an unfolded state wherein each flap extends substantially perpendicular to said holder plate on opposite sides thereof, each said flap having a beveled edge portion extending along the base thereof which engages with a mating chamber configured on the top surface portion of said holder when said flaps are in said unfolded state.

16. The holder of claim 15, wherein said serrated surface of the front edge portion of said collar is engaged with said serrated surface of said upper edge of said stopper portion of said sleeve by tubing which is tightly fit over the distal end of said sleeve to contact the distal end of said collar and push said collar into contact with said stopper portion of said sleeve.

17. A method for manufacturing a venipuncture needle having a displacement surface bridging the opening into the lumen of the needle, comprising the steps of:

forcing a point on the interior surface of a tubular, hollow shank section into contact with the radially opposite interior surface of said shank section to thereby create a substantially V-shaped channel on the outer periphery of said shank section;

grinding said tubular, hollow shank section rearwardly from the contact point of said interior surface and said radially opposite interior surface of said shank to form a pair of inclined, lateral apertures from said openings and a non-cutting smoothly inflected displacement surface from said V-shaped channel, said displacement surface extending rearwardly from said contact point.

18. The method of claim 17, further including the steps of forming bevels at the inner edges of said lateral apertures; and grinding the portions of said tubular shank immediately adjacent said contact point into a puncturing tip for the needle.

19. The method of claim 17, including further step of fixedly attaching the forwardmost end of said displacement surface to said radially opposite interior surface of said shank at said contact point.

20. The method of claim 19, wherein said attaching step includes the substep of laser beam welding the forwardmost end of said displacement surface to said radially opposite interior surface of said shank.

* * * * *